United States Patent
Kawaguchi et al.

(10) Patent No.: US 11,730,776 B2
(45) Date of Patent: Aug. 22, 2023

(54) PREVENTIVE AND/OR THERAPEUTIC AGENT FOR CLOSTRIDIUM DIFFICILE INFECTION

(71) Applicant: Nutri Co., Ltd., Mie (JP)

(72) Inventors: Susumu Kawaguchi, Mie (JP); Miho Kato, Mie (JP)

(73) Assignee: NUTRI CO., LTD., Yokkaichi (JP)

( * ) Notice: Subject to any disclaimer, the term of this patent is extended or adjusted under 35 U.S.C. 154(b) by 0 days.

(21) Appl. No.: 17/279,084

(22) PCT Filed: Oct. 4, 2019

(86) PCT No.: PCT/JP2019/039254
§ 371 (c)(1),
(2) Date: Mar. 23, 2021

(87) PCT Pub. No.: WO2020/075637
PCT Pub. Date: Apr. 16, 2020

(65) Prior Publication Data
US 2021/0386797 A1    Dec. 16, 2021

(30) Foreign Application Priority Data
Oct. 10, 2018  (JP) ................. 2018-191488

(51) Int. Cl.
*A61K 35/744* (2015.01)
*A61P 31/04* (2006.01)
*A61K 9/00* (2006.01)

(52) U.S. Cl.
CPC .......... *A61K 35/744* (2013.01); *A61K 9/0053* (2013.01); *A61P 31/04* (2018.01)

(58) Field of Classification Search
None
See application file for complete search history.

(56) References Cited

U.S. PATENT DOCUMENTS

2005/0266069 A1* 12/2005 Simmons ............. A23L 29/065
                                                      424/93.45
2016/0158295 A1    6/2016 Afeyan et al.

FOREIGN PATENT DOCUMENTS

| JP | 2002-179580 A | 6/2002 |
| JP | 2003-261453 A | 9/2003 |
| JP | 2007-320946 A | 12/2007 |
| WO | 2018/139503 A1 | 8/2018 |
| WO | WO-2019053604 A1 * | 3/2019 ........... A61K 35/747 |

OTHER PUBLICATIONS

Mansour et al. Probiotics and Antimicro. Prot. (2018) 10:511-512.*
Choi et al. Nutrients. 2016; 8(3):146 pp. 1-11.*
Gu et al. Protective Effects of Enterococcus Faecalis 2001 (EF 2001) against Radiation-Induced Leukocytes Damage in Mice. Journal of Junshin Gakuen University, Faculty of Health Sciences vol. 2, Mar. 2013.*
International Search Report issued in corresponding International Patent Application No. PCT/JP2019/039254 dated Nov. 19, 2019.
Relationship between "Intestinal flora and lifestyle-related diseases" and dietary habits, Food Industry, 44 (1): 26-29 (2000) (see International Search Report).
Yamamoto-Osaki et al., "Growth inhibition of Clostridium difficile by intestinal flora of infant faeces in continuous flow culture," Journal of Medical Microbiology, 40: 179-187 (1994).
Extended European Search Report issued in corresponding European Patent Application No. 19870609.5 dated Oct. 7, 2022.

* cited by examiner

*Primary Examiner* — Oluwatosin A Ogunbiyi
(74) *Attorney, Agent, or Firm* — Morgan, Lewis & Bockius LLP

(57) ABSTRACT

Provided is a novel prophylactic and/or therapeutic agent for *Clostridium difficile* infection. It was found that a bacterium belonging to the genus *Enterococcus* can prevent and/or treat *Clostridium difficile* infection. The prophylactic and/or therapeutic agent for *Clostridium difficile* infection, comprising a bacterium belonging to the genus *Enterococcus*. A medicine for prevention and/or treatment of *Clostridium difficile* infection, comprising a bacterium belonging to the genus *Enterococcus*. A food for prevention and/or treatment of *Clostridium difficile* infection, comprising a bacterium belonging to the genus *Enterococcus*.

18 Claims, 9 Drawing Sheets

[Figure 1]
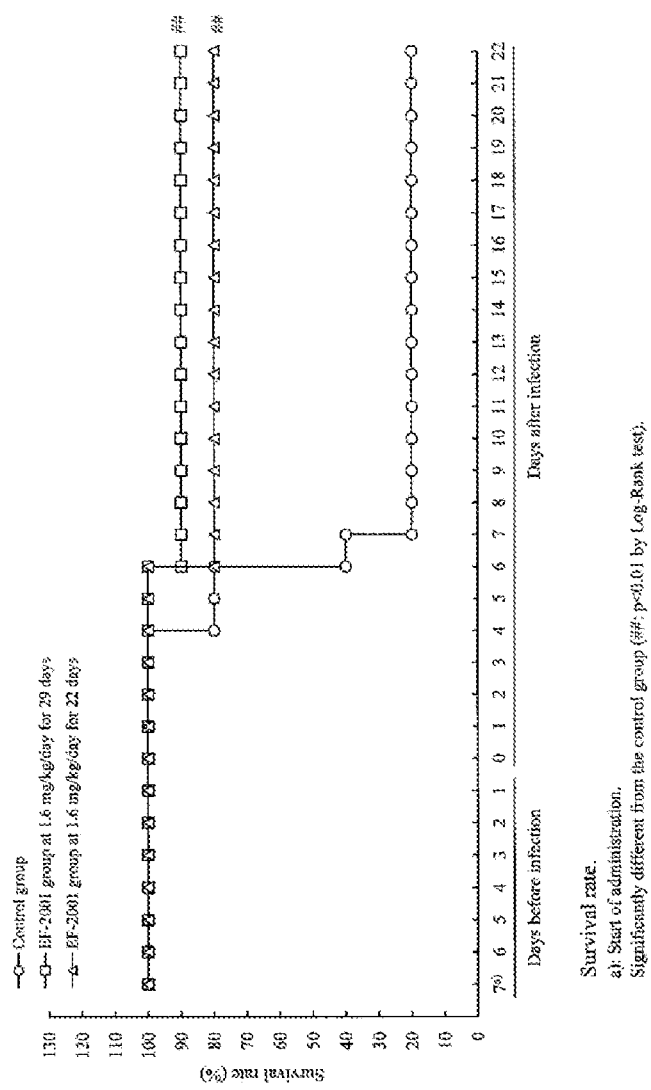

[Figure 2]
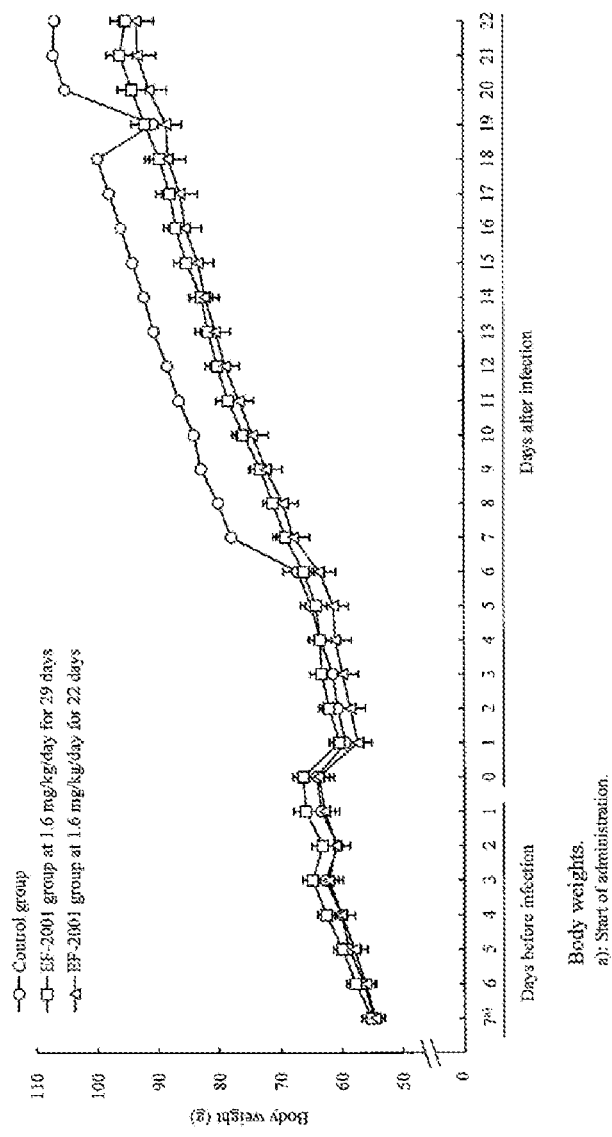

[Figure 3]
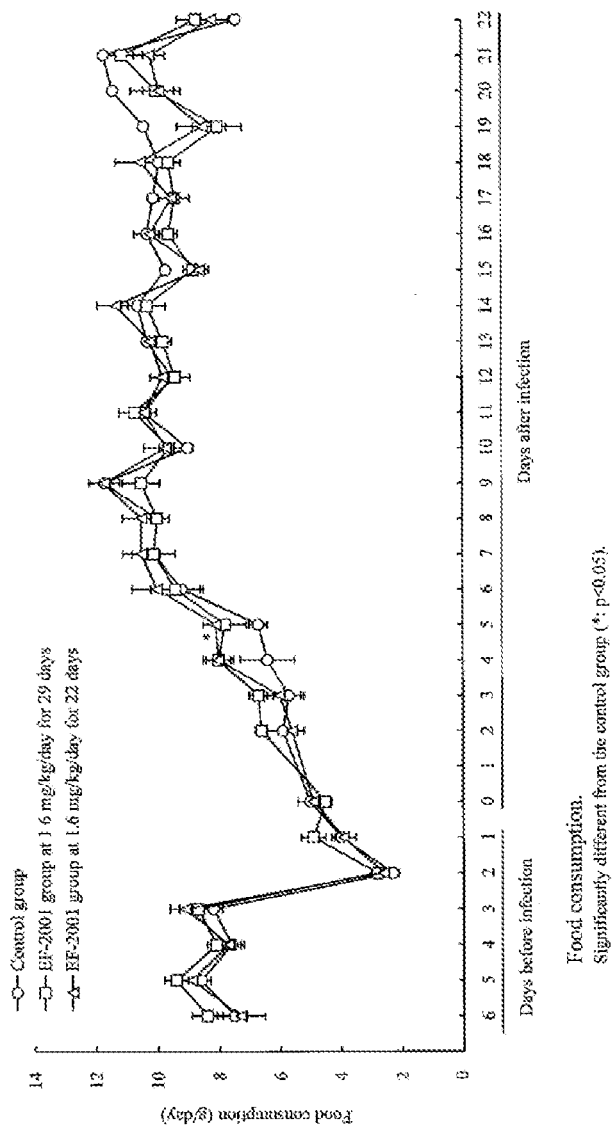

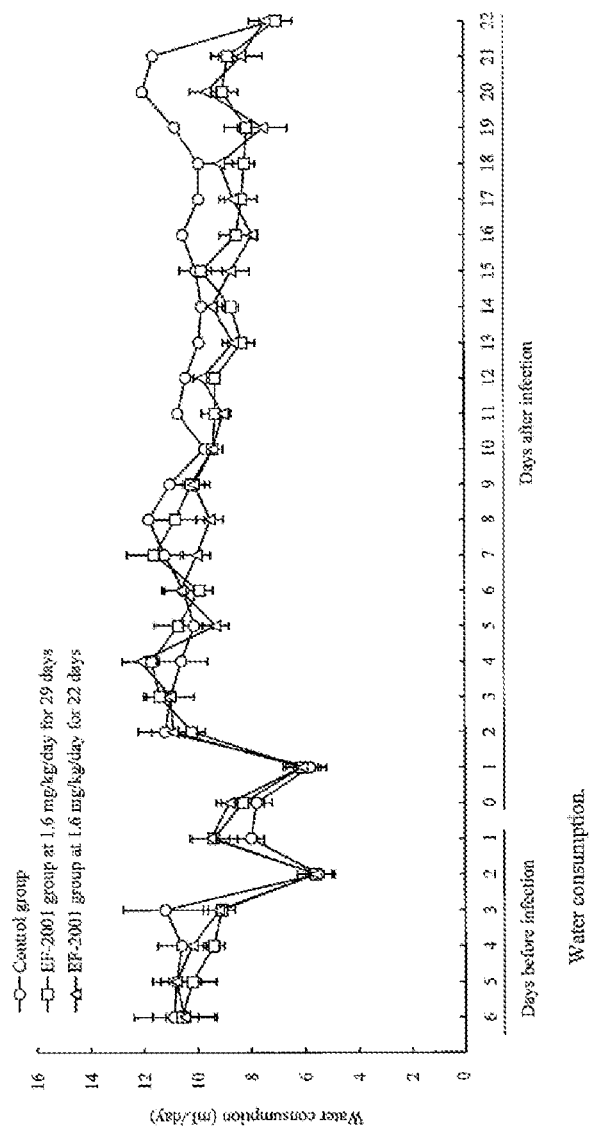
[Figure 4]

[Figure 5-1]
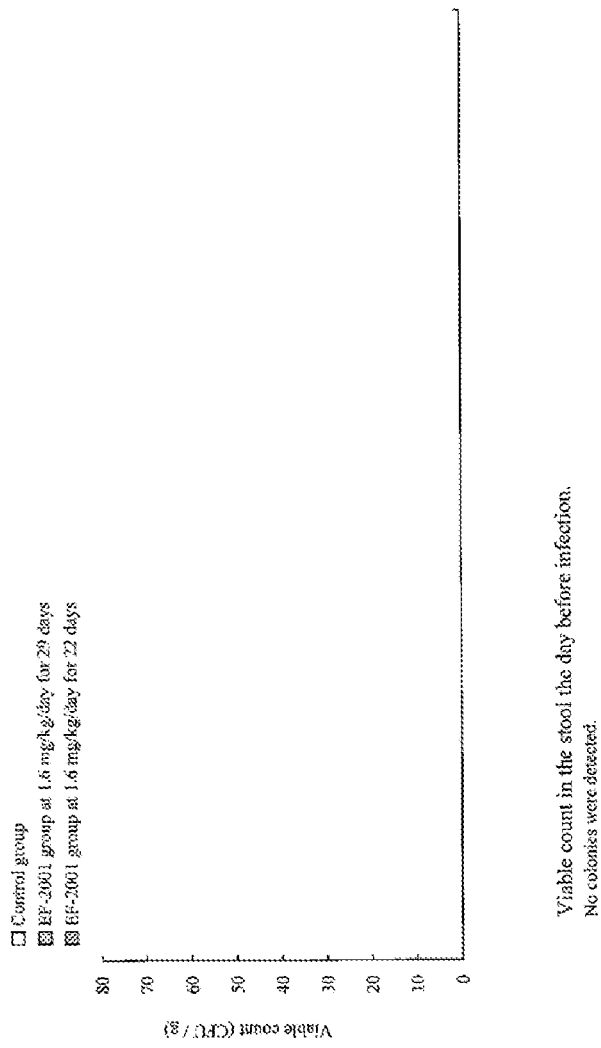

[Figure 5-2]
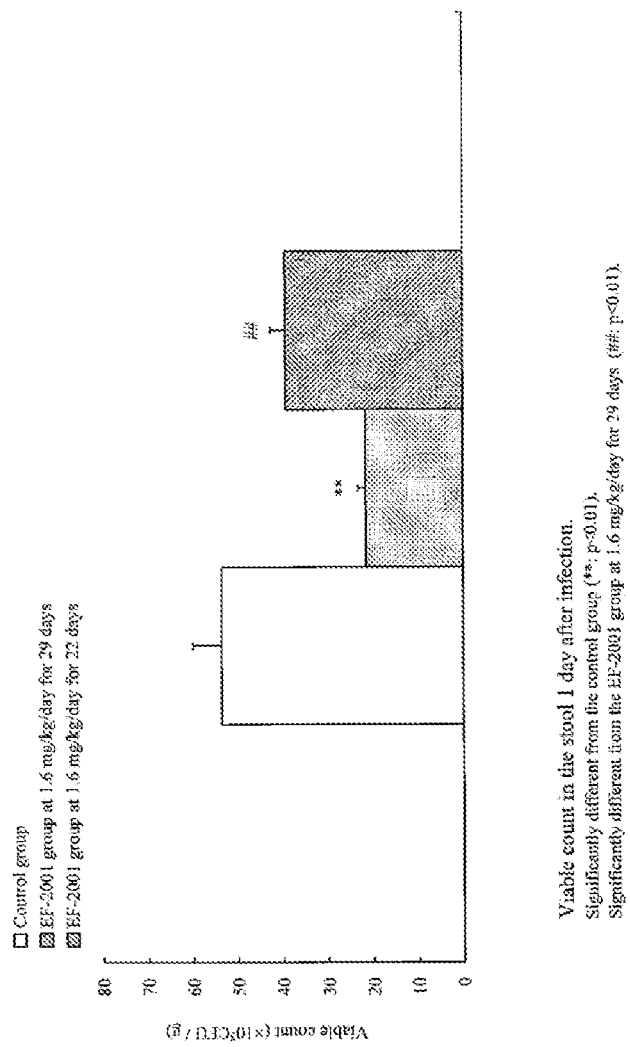

[Figure 5-3]
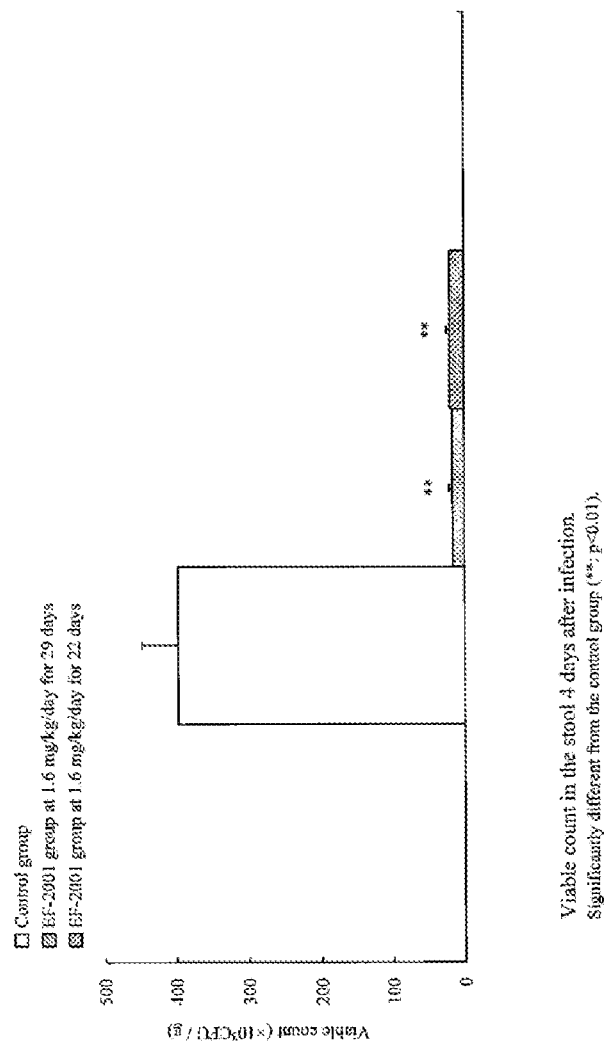

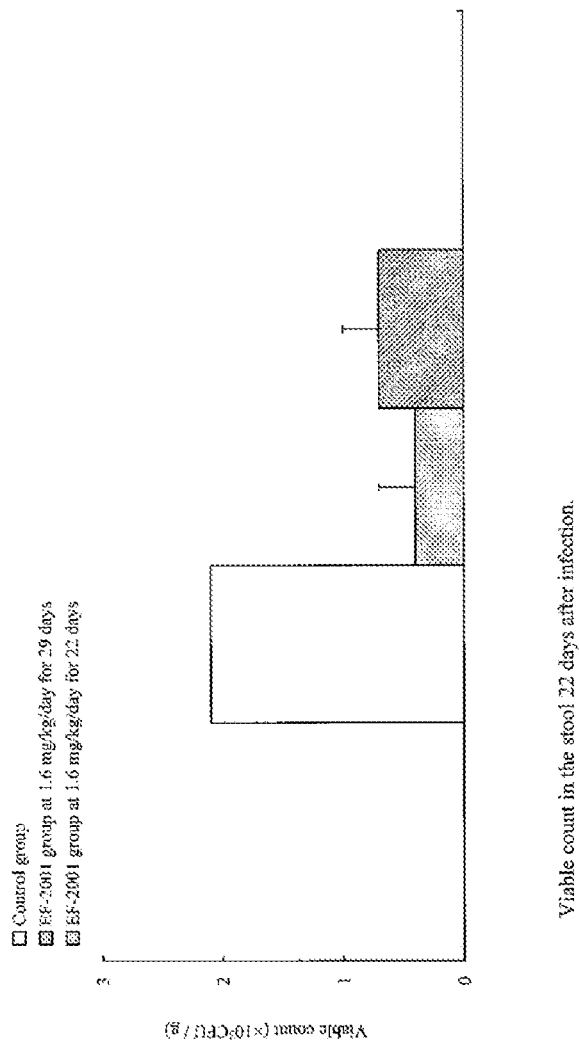
[Figure 5-4]

[Figure 6]
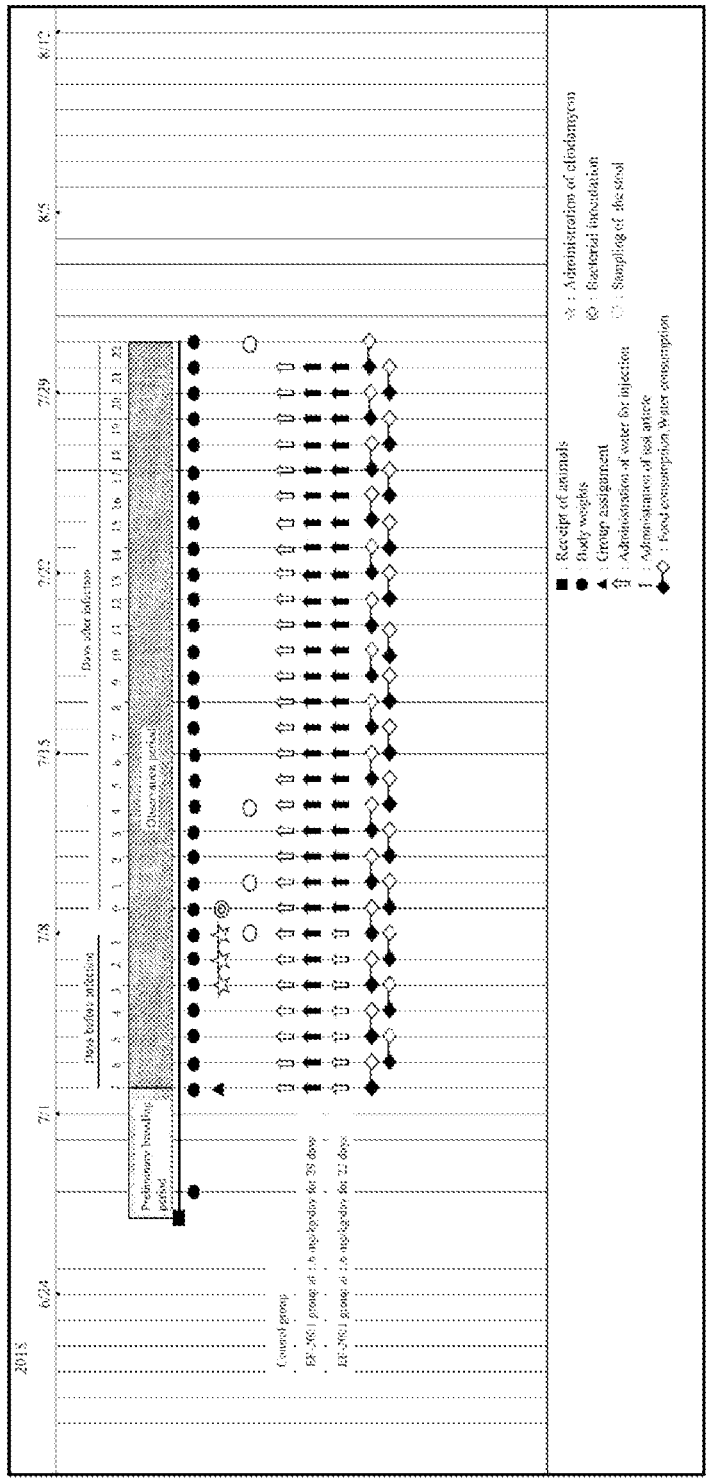

PREVENTIVE AND/OR THERAPEUTIC AGENT FOR CLOSTRIDIUM DIFFICILE INFECTION

TECHNICAL FIELD

The present invention relates to a prophylactic and/or therapeutic agent for *Clostridium difficile* infection.

BACKGROUND ART

*Clostridium difficile* infections (CDIs) often occur when the gastrointestinal flora is disrupted by use of antibiotics or some other reason. In most cases, development of CDIs is associated with use of antibiotics. Further, aging and presence or absence of underlying diseases are susceptibility factors for developing CDIs.

Most of CDIs are gastrointestinal infections, main symptoms of which are diarrhea and abdominal pain. However, sometimes CDIs are accompanied by fever and leukocytosis. When these symptoms become severe, some patients may be led to death by toxic megacolon, ileus or gastrointestinal perforation.

There are "carriers" of *Clostridium difficile* who carry *C. difficile* in the gastrointestinal tract but are asymptomatic. A large number of such "carriers" are present among hospitalized patients to whom antibiotics are frequently administered. *C. difficile* is discharged with the stool from CDI patients and asymptomatic carriers, contaminates the environment including the fingers of health care workers and medical staff, and causes a problem of health-care-associated infection. Therefore, CDI is a common infection in health care sites where a number of elderly persons who need excretion care (such as exchange of diapers) are hospitalized and yet infection control (including appropriate use of antibiotics) is not adequately performed. However, in those medical institutions where antibiotics are abused and infection control is inadequate, the levels of concern and knowledge about CDI are so low that CDI is not diagnosed appropriately and its incidence seems apparently low in many cases, which is considered to be problematic. Thus, CDI easily becomes chronic in medical institutions and elderly care facilities. Under these circumstances, the necessity for taking infection control measures is being discussed.

PRIOR ART LITERATURE

Non-Patent Documents

Non-Patent Document No. 1: Basic science and clinical aspect of *Clostridium difficile* infection, Modern Media Vol. 56, No. 10, 2010 www.eiken.co.jp/modern_media/backnumber/pdf/MM1010_01.pdf

DISCLOSURE OF THE INVENTION

Problem for Solution by the Invention

It is an object of the present invention to provide a novel, prophylactic and/or therapeutic agent for *Clostridium difficile* infection.

Means to Solve the Problem

As a result of intensive efforts, the present inventors have found that a lactic acid bacterium belonging to the genus *Enterococcus* can prevent and/or treat *Clostridium difficile* infection; the present invention has been achieved based on this finding.

The gist of the present invention is as follows.

(1) A prophylactic and/or therapeutic agent for *Clostridium difficile* infection, comprising a bacterium belonging to the genus *Enterococcus*.

(2) The prophylactic and/or therapeutic agent for *Clostridium difficile* infection of (1), wherein the bacterium belonging to the genus *Enterococcus* is a *Lactococcus*.

(3) The prophylactic and/or therapeutic agent for *Clostridium difficile* infection of (2), wherein the *Lactococcus* is *Enterococcus fecalis*.

(4) The prophylactic and/or therapeutic agent for *Clostridium difficile* infection of (3), wherein the *Enterococcus fecalis* is EF-2001 strain.

(5) The prophylactic and/or therapeutic agent for *Clostridium difficile* infection of any one of (1)-(4), wherein the bacterium belonging to the genus *Enterococcus* is killed.

(6) The prophylactic and/or therapeutic agent for *Clostridium difficile* infection of any one of (1)-(5), wherein the bacterium belonging to the genus *Enterococcus* is orally administered.

(7) The prophylactic and/or therapeutic agent for *Clostridium difficile* infection of (6), wherein the bacterium belonging to the genus *Enterococcus* is orally administered in an amount of $1\times10^8$-$1\times10^{11}$ CFU/kg body weight per dose.

(8) The prophylactic and/or therapeutic agent for *Clostridium difficile* infection of (7), wherein the bacterium belonging to the genus *Enterococcus* is orally administered one or more times per day in an amount of $1\times10^8$-$1\times10^{11}$ CFU/kg body weight per dose.

(9) The prophylactic and/or therapeutic agent for *Clostridium difficile* infection of (8), wherein the bacterium belonging to the genus *Enterococcus* is orally administered one to five times per day in an amount of $1\times10^8$-$1\times10^{11}$ CFU/kg body weight per dose.

(10) The prophylactic and/or therapeutic agent for *Clostridium difficile* infection of (6), wherein the bacterium belonging to the genus *Enterococcus* is orally administered in an amount of $1\times10^9$-$5\times10^{10}$ CFU/kg body weight per dose.

(11) The prophylactic and/or therapeutic agent for *Clostridium difficile* infection of (10), wherein the bacterium belonging to the genus *Enterococcus* is orally administered one or more times per day in an amount of $1\times10^9$-$5\times10^{10}$ CFU/kg body weight per dose.

(12) The prophylactic and/or therapeutic agent for *Clostridium difficile* infection of (11), wherein the bacterium belonging to the genus *Enterococcus* is orally administered one to five times per day in an amount of $1\times10^9$-$5\times10^{10}$ CFU/kg body weight per dose.

(13) The prophylactic and/or therapeutic agent for *Clostridium difficile* infection of (6), wherein the bacterium belonging to the genus *Enterococcus* is orally administered in an amount of $1.2\times10^{10}$ or more CFU/kg body weight per dose.

(14) The prophylactic and/or therapeutic agent for *Clostridium difficile* infection of (13), wherein the bacterium belonging to the genus *Enterococcus* is orally administered one or more times per day in an amount of $1.2\times10^{10}$ or more CFU/kg body weight per dose.

(15) The prophylactic and/or therapeutic agent for *Clostridium difficile* infection of (14), wherein the bacterium belonging to the genus *Enterococcus* is orally administered one to five times per day in an amount of $1.2 \times 10^{10}$ or more CFU/kg body weight per dose.

(16) The prophylactic and/or therapeutic agent for *Clostridium difficile* infection of any one of (6)-(15), wherein the bacterium belonging to the genus *Enterococcus* is orally administered for seven or more days.

(17) The prophylactic and/or therapeutic agent for *Clostridium difficile* infection of any one of (1)-(16), which is used for prevention of *Clostridium difficile* infection.

(18) The prophylactic and/or therapeutic agent for *Clostridium difficile* infection of any one of (1)-(16), which is used for treatment of *Clostridium difficile* infection.

(19) A medicine for prevention and/or treatment of *Clostridium difficile* infection, comprising a bacterium belonging to the genus *Enterococcus*.

(20) A food for prevention and/or treatment of *Clostridium difficile* infection, comprising a bacterium belonging to the genus *Enterococcus*.

(21) A method for prevention and/or treatment of *Clostridium difficile* infection, comprising administering to a subject a pharmaceutically effective amount of a bacterium belonging to the genus *Enterococcus*.

(22) Use of a bacterium belonging to the genus *Enterococcus* for prevention and/or treatment of *Clostridium difficile* infection.

(23) A bacterium belonging to the genus *Enterococcus* for use in a method for prevention and/or treatment of *Clostridium difficile* infection.

Effect of the Invention

The present invention enables prevention and/or treatment of *Clostridium difficile* infection.

The present specification encompasses the contents of the specification and/or drawings disclosed in Japanese Patent Application No. 2018-191488 based on which the present application claims priority.

BRIEF DESCRIPTION OF THE DRAWINGS

FIG. 1 shows test results (survival rate (results of Kaplan-Meier plot)) in Example 1.

FIG. 2 shows test results (body weight) in Example 1.

FIG. 3 shows test results (feed intake) in Example 1.

FIG. 4 shows test results (water intake) in Example 1.

FIG. 5-1 shows test results (viable cell count in the stool the day before *Clostridium difficile* ATCC43255 (hereinafter, referred to as "*C. difficile*") inoculation) in Example 1.

FIG. 5-2 shows test results (viable cell count in the stool one day after *C. difficile* inoculation) in Example 1.

FIG. 5-3 shows test results (viable cell count in the stool 4 days after *C. difficile* inoculation) in Example 1.

FIG. 5-4 shows test results (viable cell count in the stool 22 days after *C. difficile* inoculation) in Example 1.

FIG. 6 shows the test schedule in Example 1.

BEST MODES FOR CARRYING OUT THE INVENTION

Hereinafter, embodiments of the present invention will be described in more detail.

The present invention provides a prophylactic and/or therapeutic agent for *Clostridium difficile* infection, comprising a bacterium belonging to the genus *Enterococcus*.

It is recommended that the bacterium belonging to the genus *Enterococcus* be a *lactococcus* (e.g., *Enterococcus faecalis*, *Enterococcus faecium*, *Enterococcus avium*, *Enterococcus gallinarum*, or *Enterococcus casseliflavus*), and preferred is a *lactococcus* having biological response modifier (BRM) activity (YAKUGAKU ZASSHI, 112: 919-925, 1992; YAKUGAKU ZASSHI, 113: 396-399, 1992; Journal of Animal Clinical Research, 3: 11-20, 1994). *Enterococcus faecalis* is known as a *lactococcus* having BRM activity. *Enterococcus faecalis* EF-2001 strain is available from Nihon Berumu Co., Ltd. (2-14-3 Nagatacho, Chiyoda-ku, Tokyo).

*Enterococcus Faecalis*-2001 strain can be obtained from fecal matter of a normal person and has the following properties.

A Gram-positive coccus. Shape of colony (Trypto-Soya agar medium, 24-hour culture): 1.0-mm diameter, smooth, precise circle, white colony. Bacterial morphology: circular to oval (1.0×1.5 µm). Likely to form chains in liquid media. Non-spore-forming. Facultative anaerobic. Ferments glucose to produce lactic acid (final pH: 4.3). Non-gas-producing. Catalase-negative. Proliferates at 10 to 45° C. (the optimal temperature is 37° C.). Proliferates to pH 9.6, 6.5% NaCl, and 40% bile. Positive for 0.04% potassium tellurite. Positive for 0.01% tetrazolium. Positive for 0.1% methylene blue milk. Hydrolyzes arginine. Ferments amygdalin, cellobiose, fructose, galactose, glucose, glycerol, lactose, maltose, mannose, mannitol, ribose, salicin, sucrose, melicitose, and sorbitol to produce acids. Resistant at 60° C. for 30 minutes. Digests casein and gelatin. Decarboxylates tyrosine into tyramine. Lancefield antigen group: D. GC %: 35.0±1.0%.

The bacterium belonging to the genus *Enterococcus* may be a viable bacterium or a killed bacterium, and the bacterium may be subjected to a destruction treatment (e.g., homogenization, enzyme treatment, or ultrasonication) or any other treatment such as heating or drying (e.g., freeze-drying or spray-drying). The viable bacterium may be killed by heating. The viable bacterium is expected to exhibit effects produced by lactic acid fermentation. The killed bacterium is expected to exhibit an intestinal immunity-activating effect. The particle size of the bacterial cell is typically 0.05 µm-50 µm, preferably 0.08-20 µm, more preferably 0.1-10 µm. The bacterium may be mixed with a diluent, and then a thickener may be added to form granules. It is recommended to select the diluent and thickener from materials approved for addition to foods and medicines.

The prophylactic and/or therapeutic agent for *Clostridium difficile* infection of the present invention can be used for phylaxis of *Clostridium difficile* infection. As used herein, the term "phylaxis" refers to a concept encompassing not only prevention but also treatment of infection. The prophylactic and/or therapeutic agent for *Clostridium difficile* infection of the present invention can be used as a medicine or a food additive. *Clostridium difficile* may be multidrug resistant *C. difficile*.

The present invention provides a medicine for prevention and/or treatment of *Clostridium difficile* infection, comprising a bacterium belonging to the genus *Enterococcus*.

When the agent is used as a medicine, it is recommended that the bacterium belonging to the genus *Enterococcus* be used alone or be mixed with an excipient or a carrier to make a formulation such as a tablet, a capsule, a powder, a granule, a liquid, a syrup, an aerosol, a suppository, or an injection. The excipient or carrier may be any excipient or carrier that is commonly used in the art and is pharmaceutically acceptable, and the type and composition of the excipient or carrier are chosen as appropriate. For example, water or a vegetable oil is used as a liquid carrier. As a solid carrier there is used, for example, a sugar such as lactose, sucrose, or glucose, a starch such as potato starch or corn starch, or a cellulose derivative such as crystalline cellulose. A lubricant such as magnesium stearate, a binder such as gelatin or hydroxypropyl cellulose, and a disintegrant such as carboxymethyl cellulose may also be added. Further, an antioxidant, a colorant, a flavoring agent, a preservative, or the like may also be added. The medicine can also be used as a freeze-dried formulation.

The bacterium belonging to the genus *Enterococcus* can be administered by various routes, such as orally, nasally, rectally, transdermally, subcutaneously, intravenously, and intramuscularly.

The content of the bacterium belonging to the genus *Enterococcus* in the formulation varies depending on the type of the formulation, and is typically 0.001 to 100% by mass and preferably 0.01 to 100% by mass.

The dose of the bacterium belonging to the genus *Enterococcus* may be any pharmaceutically effective amount, i.e., any amount sufficient to confirm efficacy for preventing and/or treating *Clostridium difficile* infection, and it varies depending on the form of the formulation, the administration route, the age and body weight of the patient, the severity of the disease, and the like. In the case of an adult patient, for example, it is recommended to set the dose per administration to about 100,000,000 to 100,000,000,000 CFU/kg body weight, preferably about 1,000,000,000 to 50,000,000,000 CFU/kg body weight, and more preferably about 6,000,000,000 to 12,000,000,000 CFU/kg body weight, in terms of the amount of the bacterium belonging to the genus *Enterococcus*, and to give one to several (e.g., 2, 3, 4, or 5 times) administrations per day. Administration period is not particularly limited and may, for example, be 7 days or more, 10 days or more, or 17 days or more.

The bacterium belonging to the genus *Enterococcus* may be added to a food. The present invention provides a food for prevention and/or treatment of *Clostridium difficile* infection, comprising a bacterium belonging to the genus *Enterococcus*.

The following may be added to the food of the present invention: general ingredients such as protein, fat, carbohydrate, and sodium; minerals such as potassium, calcium, magnesium, and phosphorus; trace elements such as iron, zinc, copper, selenium, and chromium; vitamins such as vitamin A, β-carotene, vitamin B1, vitamin B2, vitamin B6, vitamin B12, vitamin C, niacin, folic acid, vitamin D3, vitamin E, biotin, and pantothenic acid; and other substances such as coenzyme Q10, α-lipoic acid, galacto-oligosaccharide, dietary fiber, an excipient (such as water, carboxymethyl cellulose, or lactose), a sweetener, a flavoring agent (such as malic acid, citric acid, or amino acid), and a fragrance. When the food of the present invention is provided as a liquid food, water, saline solution, fruit juice, or the like can be used as a liquid in which the food ingredients are dispersed or dissolved. In order to improve the taste in oral administration, it is recommended to use fruit juice.

The food of the present invention may be in any form such as a powder, a granule, a tablet, or a liquid. In order to allow sick or old persons to easily take the food, it is preferable for the food to be a gelled product such as jelly.

Gelling agents that can be used include thickening polysaccharides such as dextrin, agar, xanthan gum, locust bean gum, carrageenan, and pectin, gellan gum, *psyllium* seed gum, tara gum, guar gum, glucomannan, alginic acid, tamarind seed gum, and cellulose, and it is preferable to use one or two or more thickening polysaccharides. As regards the gel strength of the gelled product, it is preferable that the gel strength at 5° C. be 7,000±2,000 N/m². When the gel strength is 7,000±2,000 N/m², it is more preferable that the adhesion energy be 60±40 J/m³ and the cohesiveness be 0.7±0.1 J/m³. Such a gel with low adhesiveness and high cohesiveness has excellent swallowability.

The gel strength can be measured as follows. A texturometer of YAMADEN Co., Ltd. and a 16-mm-diameter plunger are used as gel strength measurement instruments, and the measurement is carried out under the following conditions: the measurement temperature is 25° C., the compression speed (the speed at which the plunger is pushed in) is 10 mm/s, the measurement strain (the ratio of the amount of pushing-in to the sample thickness) is 40.00%, the distance over which the plunger is pushed in is 10.00 mm, and the number of repetitions of pushing-in of the plunger is two.

The adhesion energy is measured as a negative energy required for pulling out the plunger after the first pushing-in of the plunger in the above gel strength measurement.

The cohesiveness is measured as the ratio between the energy at the first pushing-in and the energy at the second pushing-in in the above gel strength measurement.

The intake of the bacterium belonging to the genus *Enterococcus* may be any amount sufficient to confirm effectiveness for preventing and/or treating *Clostridium difficile* infection, and it varies depending on the form of the formulation, the administration route, the age and body weight of the patient, the severity of the disease, and the like. In the case of an adult patient, for example, it is recommended to set the dose per administration to about 100,000,000 to 100,000,000,000 CFU/kg body weight, preferably about 1,000,000,000 to 50,000,000,000 CFU/kg body weight, and more preferably about 6,000,000,000 to 12,000,000,000 CFU/kg body weight, in terms of the amount of the bacterium belonging to the genus *Enterococcus*, and to give one to several (e.g., about 2, 3, 4, or 5 times) administrations per day.

EXAMPLES

Hereinafter, the present invention will be described in detail based on Examples. The present invention is not limited to these Examples.

[Example 1] Phylaxis Test of Lactic Acid Bacterium EF-2001 Strain Against *C. difficile* Infection A lactic acid bacterium-containing drink was orally administered to *C. difficile* infection model, whereby the effect upon phylaxis of *C. difficile* infection was evaluated with indicators such as survival rate.
(Materials and Methods)
Test Substance and Medium
  Test substance
  Name: LACTIC ACID BACTERIA POWDER EF-2001 (Nihon Berumu Co., Ltd.) (heat-killed *E. faecalis*, 500 nm=0.5 μm in diameter)
  Properties: Yellow-brown powder
  Storage conditions: Room temperature, light-shielded, moisture-proof
  Controlled temperature: 18.0-28.0° C.
  Medium
  Name: Water for injection
  Storage Conditions: Room Temperature
  Controlled temperature: 18.0-28.0° C.
  Manufacturer: Otsuka Pharmaceutical Factory, Inc.
  Administration Sample
    Test Substance Method of Preparation Lactic acid bacteria powder EF-2001 was weighed in 20 mg (electronic balance: XP205DR, Mettler-Toledo Co., Ltd.) and suspended in water for injection. The suspension was diluted to give a total volume of 125 mL with a concentration of 0.16 mg/mL. Since the lactic acid bacteria powder precipitates, it was stirred well enough to be kept suspended. Preparation was made just before use.

Pathogenic Microorganism

Strain used

*Clostridium difficile* (ATCC43255, hereinafter, referred to as "*C. difficile*")

Storage conditions

Cryopreserved in an Ultra-cold freezer (controlled temperature: −90 to −70° C., MDF-394AT, Sanyo Electric Co., Ltd.) until use.

Reagents (1) GAM agar medium (Nissui Pharmaceutical Co., Ltd.)
(2) GAM broth medium (Nissui Pharmaceutical Co., Ltd.)
(3) Physiological saline (Otsuka Pharmaceutical Plant, Inc.)

Preculture

The preserved strain of *C. difficile* was thawed and inoculated into GAM agar medium. The resultant medium was transferred into a deoxidant-filled anaerobic jar, and then cultured in an incubator (ILE800, Yamato Scientific Co., Ltd.) set at 37° C. for 5 days. After culture, colonies were collected and added to GAM broth medium. The resultant medium was transferred into a deoxidant-filled anaerobic jar, and cultured in an incubator set at 37° C. for 2 days. The resultant culture broth served as an inoculation stock solution.

Preparation of a Liquid Bacterial Inoculum and Confirmation of Viable Cell Count The stock solution diluted 10-folds with physiological saline was used as a liquid bacterial inoculum.

Confirmation of viable cell count was performed as follows. Briefly, an aliquot of liquid bacterial inoculum was taken, diluted appropriately with physiological saline, and smeared on GAM agar medium. Then, the medium was transferred into a deoxidant-filled anaerobic jar, and cultured in an incubator set at 37° C. for 5 days. The number of colonies after culture was counted with a handy colony counter (CC-1, Azwan Co., Ltd.), and the number of viable bacterial cells contained in 1 ml of the liquid bacterial inoculum was calculated. As a result, the viable cell count in the liquid bacterial inoculum was $3.5 \times 10^5$ CFU/mL.

Animal Test System

Animal Species, Lineage

Species: Hamster (SPF)

Lineage: Slc:syrian

Sex, age, and number of animals acquired

Male, 3 weeks old, 33 hamsters

Body Weight Range 1 Day after Acquisition of Animals 40.8-58.0 g

Source

Japan SLC, Inc.

Preliminary Feeding

The animals were preliminarily fed for five days. During this period, their general condition was observed once a day and the body weight was measured twice (one day after the acquisition of animals and the final day of preliminary feeding) by electronic balance (MS3002S/02, Metler Toledo Inc.). Animals with no abnormalities in body weight change and general condition were used for grouping.

Grouping Methods

The animals were stratified by body weight using a computer program (IBUKI, Nihon Bioresearch Inc.) and then at the day of grouping, random sampling was applied to ensure that the mean body weight and variance of the respective groups were approximately equal.

Identification Methods

Animals were identified at the day of their acquisition by painting colors on their back and limbs with oil-based ink. After grouping, the animals were identified by painting colors on their back and limbs using oil-based ink of the same color as each label. Each cage was fitted with two kinds of label, one being applied during the preliminary feeding period and filled with test number, date of animal acquisition, and animal number for preliminary feeding, and the other being color-coded labels applied after grouping and filled with test number, group name, and animal number.

Environmental Conditions and Rearing Management

Animals were reared in a room (Kiso Sansen Branch, Room No. 2) maintained at a temperature of 18-28° C. (measured value: 19-25° C.), a humidity of 30-80% (measured value: 47-65%), and light/dark periods, each 12 hours (lighting applied: 6:00 a.m. to 6:00 p.m.). Animals were reared individually in plastic cages (W: 175×D: 245×H: 125 mm) each equipped with a metal drainboard both during the preliminary feeding period and after grouping.

Cages, feeders and metal drainboards were changed at least once a week, and water bottles were changed at least twice a week. The room was cleaned up daily by wiping and disinfecting the floor with a disinfectant-soaked mop. After completion of rearing, the room was spray-disinfected with Actril™ (Minntech Corporation).

Feed

The animals were fed ad libitum with a γ-ray irradiated diet (30 kGy-irradiated CRF-1; Oriental Yeast Co., Ltd.) placed in feeders; the diet was manufactured within 5 months before the experiment. However, animals were fasted for 20 hours after injection of the liquid bacterial inoculum.

Contaminant levels, bacterial counts, and nutrient contents of the diet before γ-ray irradiation were confirmed to meet the acceptance criteria of the test facility for each lot of the diet.

Drinking Water

Chlorine/hydrochloric acid in water [1 L of autoclave treated (121° C., 15 min) tap water supplemented with 1 mL of 5% sodium hypochlorite (Baigenlux; Kazusa Co., Ltd.) and 7 mL of hydrochloric acid (1 N; FUJIFILM Wako Pure Chemical Corporation)] was put in water supply bottles, and animals were allowed to drink ad libitum. Contaminant levels of tap water were analyzed almost every 6 months to ensure that they met the acceptance criteria of the test facility.

Administration

Route of Administration: Oral

Administration Method rat

A 1 mL or 2.5 mL disposable syringe (Terumo Co., Ltd.) equipped with a rat feeding needle (FUCHIGAMI) was used to perform forced oral administration. At the time of administration, the required amount was collected by stirring the sample.

Dosage Volume, Time of Administration, Number of Doses, and Period of Administration Dosage volume: A dose of 10 mL/kg was determined by calculation based on the body weight of animal on the day of administration.

Time of administration: The administration was started at 11:00 a.m. and continued sequentially beginning from Group 1.

Number of doses: Every group received once-daily administration.

Administration period: The day when administration started was regarded as day 1. Groups 1 and 2 received administration for 7 days before inoculation and for 22 days from the day of inoculation (Group 1 received water for injection). Group 3 received administration for 22 days from the day of inoculation. However, this Group received water for injection for 7 days before inoculation.

Grouping

The number of animals and group composition are shown in the table below.

| Group | Group name | Color of label | Dose (mg/kg/day) | Test Substance Administration Period | Number of animals (animal number) |
|---|---|---|---|---|---|
| 1 | CONTROL (0 mg/125 mL) | White | 0* | 29 days including pre- and post- inoculation periods | 10 (M01101-M01110) |
| 2 | LACTIC ACID BACTERIA POWDER EF-2001 (80 mg/125 mL) Whole-period administration | Red | 1.6 | 29 days including pre- and post-inoculation periods | 10 (M02201-M02210) |
| 3 | LACTIC ACID BACTERIA POWDER EF-2001 (80 mg/125 mL) Post-inoculation administration | Blue | 1.6 | 22 days from the day of inoculation** | 10 (M03301-M03310) |

*The medium, water for injection, was administered.
**For 7 days before inoculation, water for injection was administered once per day.
Administration to animals with lactic acid bacteria powder EF-2001 at a dose of 80 mg/125 mL once a day is equivalent to a dose of $1.2 \times 10^{10}$ CFU/kg/day.

Method of Clindamycin Administration and Method of Inoculation of Bacterial Solution Three days before inoculation, clindamycin (Dalacin™ S for injection 300 mg; Pfizer) was administered intraperitoneally at 100 mg/kg (liquid volume: 10 mL/kg) before administration of the test substance and the medium, and this practice was repeated for the following 2 days. The day after the final administration of clindamycin, 1 mL of the liquid bacterial inoculum was administered orally. The bacterial inoculum was stirred for use in each inoculation. Inoculation was performed 2 hours before administration of the test substance.

Observation and Examination

Observation of general condition

The general condition of the animals was observed once a day before the administration of the test substance or the medium, for the period from the day of grouping to the day before the inoculation. For the period from the day of inoculation to day 10 post-inoculation, the general condition was observed 4 times a day (i.e., twice in the morning and twice in the afternoon). At day 11 post-inoculation and thereafter, the general condition was observed twice a day (i.e., once in the morning and once in the afternoon). On the day, the first observation in the morning was performed before the inoculation.

Measurement of Body Weight

After the beginning of administration, body weight was measured every day with an electronic balance (MS3002S/02, ME3002, Mettler-Toledo Co., Ltd.)

Measurement of Feed Intake and Water Intake

Following the day of grouping, the amounts of feed and water inclusive of the feeder and water supply bottle were measured every day with an electronic balance (MS3002S/02, ME3002, Mettler-Toledo Co., Ltd.) and the amounts remaining in the feeder and water supply bottle were measured on the following day. Feed intake (or water intake) per day was calculated from the difference between the amount of feed (or water) and the amount remaining in the feeder (or water supply bottle).

Humanitarian End Point

At day 4 post-inoculation, serious conditions (recumbency and hypothermia) were recognized in M01101 and M01106, which were euthanized under anesthesia with isoflurane.

Stool Collection and Measurement of Bacterial Cell Count in the Stool

The stool was collected from all the surviving animals in centrifugal tubes the day before inoculation, day 1 post-inoculation, day 4 post-inoculation, and on the final day of observation. After collection, the weight of the stool was measured (electronic balance ME204; Mettler-Toledo Co., Ltd.). PBS (2 mL) was added to the stool for suspension. Using the resultant suspension as a stock solution, $10^2$- and $10^4$-fold dilutions were prepared with PBS. A 100 μl aliquot was taken from the stock solution and each of the dilutions, and smeared on CCFA medium (Becton Dickinson Japan). This medium was transferred into a deoxidant-filled anaerobic jar, and cultured in an incubator set at 37° C. for 5 days. The number of colonies after culture was counted with a handy colony counter (CC-1, Azwan Co., Ltd.). The applicable number of colonies was calculated from the maximum dilution ratio at which colony counting was possible.

Statistical Methods

The survival rate was calculated for each group. For the body weight, feed intake, water intake, and the bacterial cell count in the stool, the average and standard deviation in each group were calculated.

A Fisher's exact test was used as a significance test for the survival rate on each day of observation as between the control group and each of the other groups. A Kaplan-Meier plot was drawn and Logrank test was conducted over the entire observation period, and generalized Wilcoxon test was conducted, with Holm corrections being made for comparisons between groups to adjust for multiplicity.

Multiple comparisons were performed as a significance test for the body weight, feed intake, water intake and the bacterial cell count in the stool. That is, a test of equal variance by Bartlett method was carried out, and Tukey's test was carried out in the case of equal variance. On the other hand, when no equal variance was observed, Steel-Dwass test was used.

A hazard rate of 5% was considered significant, and separate indications were given for a hazard rate less than 5% and a hazard rate less than 1%.

A commercially available statistical program (SAS system; SAS Institute Japan) was used for the statistical analyses.

(Test Results)
General Condition

The results of observation are shown in Table 1. For survival rate, Kaplan-Meier plots are shown in FIG. 1.

In the control group, loose stool was observed from day 1 post-inoculation and piloerection from day 3 post-inoculation. Since two animals became moribund at day 4 post-inoculation, they were euthanized. Death was seen in four animals at day 6 post-inoculation and two animals at day 7 post-inoculation. Survival rate at day 22 post-inoculation was 20%.

In the whole-period administration group, loose stool and piloerection were observed as in the control group, but with fewer cases of piloerection. One animal died at day 7 post-inoculation. Survival rate at day 22 post-inoculation was 90%. In comparison with the control group, significantly high values (Fisher's exact test) were observed at day 6 post-inoculation and thereafter, and significantly high values were also observed over the whole observation period (Logrank test).

In the post-inoculation administration group, loose stool and piloerection were observed as in the control group, but with fewer cases of piloerection. Two animals died at day 7 post-inoculation. Survival rate at day 22 post-inoculation was 80%. In comparison with the control group, significantly high values (Fisher's exact test) were observed at day 6 post-inoculation and thereafter, and significantly high values were also observed over the whole observation period (Logrank test).

TABLE 1

Clinical signs

| Group | Dose (mg/kg/day) | Period for administration | Number of animals and clinical signs | Days before infection |  |  |  |  |  |  |
|---|---|---|---|---|---|---|---|---|---|---|
|  |  |  |  | 7[a] | 6 | 5 | 4 | 3 | 2 | 1 |
| Control | 0 | 29 | Number of animals | 10 | 10 | 10 | 10 | 10 | 10 | 10 |
|  |  |  | Normal | 10 | 10 | 10 | 10 | 10 | 10 | 10 |
|  |  |  | Loose stool | 0 | 0 | 0 | 0 | 0 | 0 | 0 |
|  |  |  | Coarse fur | 0 | 0 | 0 | 0 | 0 | 0 | 0 |
|  |  |  | Moribundity | 0 | 0 | 0 | 0 | 0 | 0 | 0 |
|  |  |  | Death | 0 | 0 | 0 | 0 | 0 | 0 | 0 |
| EF-2001 | 1.6 | 29 | Number of animals | 10 | 10 | 10 | 10 | 10 | 10 | 10 |
|  |  |  | Normal | 10 | 10 | 10 | 10 | 10 | 10 | 10 |
|  |  |  | Loose stool | 0 | 0 | 0 | 0 | 0 | 0 | 0 |
|  |  |  | Coarse fur | 0 | 0 | 0 | 0 | 0 | 0 | 0 |
|  |  |  | Death | 0 | 0 | 0 | 0 | 0 | 0 | 0 |
|  |  | 22 | Number of animals | 10 | 10 | 10 | 10 | 10 | 10 | 10 |
|  |  |  | Normal | 10 | 10 | 10 | 10 | 10 | 10 | 10 |
|  |  |  | Loose stool | 0 | 0 | 0 | 0 | 0 | 0 | 0 |
|  |  |  | Coarse fur | 0 | 0 | 0 | 0 | 0 | 0 | 0 |
|  |  |  | Death | 0 | 0 | 0 | 0 | 0 | 0 | 0 |

| Group | Dose (mg/kg/day) | Period for administration | Number of animals and clinical signs | Days after infection | | | | | | | |
|---|---|---|---|---|---|---|---|---|---|---|---|
|  |  |  |  | 0 | | | | 1 | | | |
|  |  |  |  | AM1 | AM2 | PM1 | PM2 | AM1 | AM2 | PM1 | PM2 |
| Control | 0 | 29 | Number of animals | 10 | 10 | 10 | 10 | 10 | 10 | 10 | 10 |
|  |  |  | Normal | 10 | 10 | 10 | 10 | 0 | 0 | 0 | 0 |
|  |  |  | Loose stool | 0 | 0 | 0 | 0 | 10 | 10 | 10 | 10 |
|  |  |  | Coarse fur | 0 | 0 | 0 | 0 | 0 | 0 | 0 | 0 |
|  |  |  | Moribundity | 0 | 0 | 0 | 0 | 0 | 0 | 0 | 0 |
|  |  |  | Death | 0 | 0 | 0 | 0 | 0 | 0 | 0 | 0 |
| EF-2001 | 1.6 | 29 | Number of animals | 10 | 10 | 10 | 10 | 10 | 10 | 10 | 10 |
|  |  |  | Normal | 10 | 10 | 10 | 10 | 0 | 0 | 0 | 0 |
|  |  |  | Loose stool | 0 | 0 | 0 | 0 | 10 | 10 | 10 | 10 |
|  |  |  | Coarse fur | 0 | 0 | 0 | 0 | 0 | 0 | 0 | 0 |
|  |  |  | Death | 0 | 0 | 0 | 0 | 0 | 0 | 0 | 0 |
|  |  | 22 | Number of animals | 10 | 10 | 10 | 10 | 10 | 10 | 10 | 10 |
|  |  |  | Normal | 10 | 10 | 10 | 10 | 0 | 0 | 0 | 0 |
|  |  |  | Loose stool | 0 | 0 | 0 | 0 | 10 | 10 | 10 | 10 |
|  |  |  | Coarse fur | 0 | 0 | 0 | 0 | 0 | 0 | 0 | 0 |
|  |  |  | Death | 0 | 0 | 0 | 0 | 0 | 0 | 0 | 0 |

| Group | Dose (mg/kg/day) | Period for administration | Number of animals and clinical signs | Days after infection | | | | | | | |
|---|---|---|---|---|---|---|---|---|---|---|---|
|  |  |  |  | 2 | | | | 3 | | | |
|  |  |  |  | AM1 | AM2 | PM1 | PM2 | AM1 | AM2 | PM1 | PM2 |
| Control | 0 | 29 | Number of animals | 10 | 10 | 10 | 10 | 10 | 10 | 10 | 10 |
|  |  |  | Normal | 0 | 0 | 0 | 0 | 0 | 0 | 0 | 0 |
|  |  |  | Loose stool | 10 | 10 | 10 | 10 | 10 | 10 | 10 | 10 |
|  |  |  | Coarse fur | 0 | 0 | 0 | 0 | 2 | 2 | 10 | 10 |
|  |  |  | Moribundity | 0 | 0 | 0 | 0 | 0 | 0 | 0 | 0 |

TABLE 1-continued

Clinical signs

| Group | Dose (mg/kg/day) | Period for administration | Number of animals and clinical signs | | | | | | | | |
|---|---|---|---|---|---|---|---|---|---|---|---|
| EF-2001 | 1.6 | 29 | Death | 0 | 0 | 0 | 0 | 0 | 0 | 0 | 0 |
|  |  |  | Number of animals | 10 | 10 | 10 | 10 | 10 | 10 | 10 | 10 |
|  |  |  | Normal | 0 | 0 | 0 | 0 | 0 | 0 | 0 | 0 |
|  |  |  | Loose stool | 10 | 10 | 10 | 10 | 10 | 10 | 10 | 10 |
|  |  |  | Coarse fur | 0 | 0 | 0 | 0 | 0 | 0 | 0 | 0 |
|  |  |  | Death | 0 | 0 | 0 | 0 | 0 | 0 | 0 | 0 |
|  |  | 22 | Number of animals | 10 | 10 | 10 | 10 | 10 | 10 | 10 | 10 |
|  |  |  | Normal | 0 | 0 | 0 | 0 | 0 | 0 | 0 | 0 |
|  |  |  | Loose stool | 10 | 10 | 10 | 10 | 10 | 10 | 10 | 10 |
|  |  |  | Coarse fur | 0 | 0 | 0 | 0 | 0 | 0 | 0 | 0 |
|  |  |  | Death | 0 | 0 | 0 | 0 | 0 | 0 | 0 | 0 |

| Group | Dose (mg/kg/day) | Period for administration | Number of animals and clinical signs | Days after infection | | | | | | | |
|---|---|---|---|---|---|---|---|---|---|---|---|
|  |  |  |  | 4 | | | | 5 | | | |
|  |  |  |  | AM1 | AM2 | PM1 | PM2 | AM1 | AM2 | PM1 | PM2 |
| Control | 0 | 29 | Number of animals | 10 | 8 | 8 | 8 | 8 | 8 | 8 | 8 |
|  |  |  | Normal | 0 | 0 | 0 | 0 | 0 | 0 | 0 | 0 |
|  |  |  | Loose stool | 8 | 8 | 8 | 8 | 8 | 8 | 8 | 8 |
|  |  |  | Coarse fur | 8 | 8 | 8 | 8 | 8 | 8 | 8 | 8 |
|  |  |  | Moribundity | 2 | 0 | 0 | 0 | 0 | 0 | 0 | 0 |
|  |  |  | Death | 0 | 0 | 0 | 0 | 0 | 0 | 0 | 0 |
| EF-2001 | 1.6 | 29 | Number of animals | 10 | 10 | 10 | 10 | 10 | 10 | 10 | 10 |
|  |  |  | Normal | 0 | 0 | 0 | 0 | 0 | 0 | 0 | 0 |
|  |  |  | Loose stool | 10 | 10 | 10 | 10 | 10 | 10 | 10 | 10 |
|  |  |  | Coarse fur | 0 | 0 | 0 | 0 | 1 | 1 | 1 | 1 |
|  |  |  | Death | 0 | 0 | 0 | 0 | 0 | 0 | 0 | 0 |
|  |  | 22 | Number of animals | 10 | 10 | 10 | 10 | 10 | 10 | 10 | 10 |
|  |  |  | Normal | 0 | 0 | 0 | 0 | 0 | 0 | 0 | 0 |
|  |  |  | Loose stool | 10 | 10 | 10 | 10 | 10 | 10 | 10 | 10 |
|  |  |  | Coarse fur | 2 | 2 | 2 | 2 | 2 | 2 | 2 | 2 |
|  |  |  | Death | 0 | 0 | 0 | 0 | 0 | 0 | 0 | 0 |

| Group | Dose (mg/kg/day) | Period for administration | Number of animals and clinical signs | Days after infection | | | | | | | |
|---|---|---|---|---|---|---|---|---|---|---|---|
|  |  |  |  | 6 | | | | 7 | | | |
|  |  |  |  | AM1 | AM2 | PM1 | PM2 | AM1 | AM2 | PM1 | PM2 |
| Control | 0 | 29 | Number of animals | 8 | 8 | 8 | 4 | 4 | 2 | 2 | 2 |
|  |  |  | Normal | 0 | 0 | 0 | 0 | 0 | 0 | 0 | 0 |
|  |  |  | Loose stool | 8 | 8 | 4 | 4 | 2 | 2 | 2 | 2 |
|  |  |  | Coarse fur | 8 | 8 | 4 | 4 | 0 | 0 | 0 | 0 |
|  |  |  | Moribundity | 0 | 0 | 0 | 0 | 0 | 0 | 0 | 0 |
|  |  |  | Death | 0 | 0 | 4 | 0 | 2 | 0 | 0 | 0 |
| EF-2001 | 1.6 | 29 | Number of animals | 10 | 10 | 10 | 10 | 10 | 9 | 9 | 9 |
|  |  |  | Normal | 0 | 0 | 0 | 0 | 0 | 0 | 0 | 0 |
|  |  |  | Loose stool | 10 | 10 | 10 | 10 | 9 | 9 | 9 | 9 |
|  |  |  | Coarse fur | 1 | 1 | 1 | 1 | 0 | 0 | 0 | 0 |
|  |  |  | Death | 0 | 0 | 0 | 0 | 1 | 0 | 0 | 0 |
|  |  | 22 | Number of animals | 10 | 10 | 10 | 10 | 10 | 8 | 8 | 8 |
|  |  |  | Normal | 0 | 0 | 0 | 0 | 0 | 0 | 0 | 0 |
|  |  |  | Loose stool | 10 | 10 | 10 | 10 | 8 | 8 | 8 | 8 |
|  |  |  | Coarse fur | 2 | 2 | 2 | 2 | 0 | 0 | 0 | 0 |
|  |  |  | Death | 0 | 0 | 0 | 0 | 2 | 0 | 0 | 0 |

| Group | Dose (mg/kg/day) | Period for administration | Number of animals and clinical signs | Days after infection | | | | | | | | | | | |
|---|---|---|---|---|---|---|---|---|---|---|---|---|---|---|---|
|  |  |  |  | 8 | | | | 9 | | | | 10 | | | |
|  |  |  |  | AM1 | AM2 | PM1 | PM2 | AM1 | AM2 | PM1 | PM2 | AM1 | AM2 | PM1 | PM2 |
| Control | 0 | 29 | Number of animals | 2 | 2 | 2 | 2 | 2 | 2 | 2 | 2 | 2 | 2 | 2 | 2 |
|  |  |  | Normal | 2 | 2 | 2 | 2 | 2 | 2 | 2 | 2 | 2 | 2 | 2 | 2 |
|  |  |  | Loose stool | 0 | 0 | 0 | 0 | 0 | 0 | 0 | 0 | 0 | 0 | 0 | 0 |
|  |  |  | Coarse fur | 0 | 0 | 0 | 0 | 0 | 0 | 0 | 0 | 0 | 0 | 0 | 0 |
|  |  |  | Moribundity | 0 | 0 | 0 | 0 | 0 | 0 | 0 | 0 | 0 | 0 | 0 | 0 |
|  |  |  | Death | 0 | 0 | 0 | 0 | 0 | 0 | 0 | 0 | 0 | 0 | 0 | 0 |
| EF-2001 | 1.6 | 29 | Number of animals | 9 | 9 | 9 | 9 | 9 | 9 | 9 | 9 | 9 | 9 | 9 | 9 |
|  |  |  | Normal | 9 | 9 | 9 | 9 | 9 | 9 | 9 | 9 | 9 | 9 | 9 | 9 |
|  |  |  | Loose stool | 0 | 0 | 0 | 0 | 0 | 0 | 0 | 0 | 0 | 0 | 0 | 0 |
|  |  |  | Coarse fur | 0 | 0 | 0 | 0 | 0 | 0 | 0 | 0 | 0 | 0 | 0 | 0 |
|  |  |  | Death | 0 | 0 | 0 | 0 | 0 | 0 | 0 | 0 | 0 | 0 | 0 | 0 |
|  |  | 22 | Number of animals | 8 | 8 | 8 | 8 | 8 | 8 | 8 | 8 | 8 | 8 | 8 | 8 |
|  |  |  | Normal | 8 | 8 | 8 | 8 | 8 | 8 | 8 | 8 | 8 | 8 | 8 | 8 |
|  |  |  | Loose stool | 0 | 0 | 0 | 0 | 0 | 0 | 0 | 0 | 0 | 0 | 0 | 0 |

TABLE 1-continued

| | | | | Clinical signs | | | | | | | | | | | | |
|---|---|---|---|---|---|---|---|---|---|---|---|---|---|---|---|---|
| | | | Coarse fur | 0 | 0 | 0 | 0 | 0 | 0 | 0 | 0 | 0 | 0 | 0 | 0 |
| | | | Death | 0 | 0 | 0 | 0 | 0 | 0 | 0 | 0 | 0 | 0 | 0 | 0 |

| | | Period for | Number of | Days after infection | | | | | | | | | | | |
|---|---|---|---|---|---|---|---|---|---|---|---|---|---|---|---|
| | Dose | adminis- | animals and | 11 | | 12 | | 13 | | 14 | | 15 | | 16 | |
| Group | (mg/kg/day) | tration | clinical signs | AM | PM | AM | PM | AM | PM | AM | PM | AM | PM | AM | PM |
| Control | 0 | 29 | Number of animals | 2 | 2 | 2 | 2 | 2 | 2 | 2 | 2 | 2 | 2 | 2 | 2 |
| | | | Normal | 2 | 2 | 2 | 2 | 2 | 2 | 2 | 2 | 2 | 2 | 2 | 2 |
| | | | Loose stool | 0 | 0 | 0 | 0 | 0 | 0 | 0 | 0 | 0 | 0 | 0 | 0 |
| | | | Coarse fur | 0 | 0 | 0 | 0 | 0 | 0 | 0 | 0 | 0 | 0 | 0 | 0 |
| | | | Moribundity | 0 | 0 | 0 | 0 | 0 | 0 | 0 | 0 | 0 | 0 | 0 | 0 |
| | | | Death | 0 | 0 | 0 | 0 | 0 | 0 | 0 | 0 | 0 | 0 | 0 | 0 |
| EF-2001 | 1.6 | 29 | Number of animals | 9 | 9 | 9 | 9 | 9 | 9 | 9 | 9 | 9 | 9 | 9 | 9 |
| | | | Normal | 9 | 9 | 9 | 9 | 9 | 9 | 9 | 9 | 9 | 9 | 9 | 9 |
| | | | Loose stool | 0 | 0 | 0 | 0 | 0 | 0 | 0 | 0 | 0 | 0 | 0 | 0 |
| | | | Coarse fur | 0 | 0 | 0 | 0 | 0 | 0 | 0 | 0 | 0 | 0 | 0 | 0 |
| | | | Death | 0 | 0 | 0 | 0 | 0 | 0 | 0 | 0 | 0 | 0 | 0 | 0 |
| | | 22 | Number of animals | 8 | 8 | 8 | 8 | 8 | 8 | 8 | 8 | 8 | 8 | 8 | 8 |
| | | | Normal | 8 | 8 | 8 | 8 | 8 | 8 | 8 | 8 | 8 | 8 | 8 | 8 |
| | | | Loose stool | 0 | 0 | 0 | 0 | 0 | 0 | 0 | 0 | 0 | 0 | 0 | 0 |
| | | | Coarse fur | 0 | 0 | 0 | 0 | 0 | 0 | 0 | 0 | 0 | 0 | 0 | 0 |
| | | | Death | 0 | 0 | 0 | 0 | 0 | 0 | 0 | 0 | 0 | 0 | 0 | 0 |

| | | Period for | Number of | Days after infection | | | | | | | | | | | |
|---|---|---|---|---|---|---|---|---|---|---|---|---|---|---|---|
| | Dose | adminis- | animals and | 17 | | 18 | | 19 | | 20 | | 21 | | 22 | |
| Group | (mg/kg/day) | tration | clinical signs | AM | PM | AM | PM | AM | PM | AM | PM | AM | PM | AM | PM |
| Control | 0 | 29 | Number of animals | 2 | 2 | 2 | 2 | 2 | 2 | 2 | 2 | 2 | 2 | 2 | 2 |
| | | | Normal | 2 | 2 | 2 | 2 | 2 | 2 | 2 | 2 | 2 | 2 | 2 | 2 |
| | | | Loose stool | 0 | 0 | 0 | 0 | 0 | 0 | 0 | 0 | 0 | 0 | 0 | 0 |
| | | | Coarse fur | 0 | 0 | 0 | 0 | 0 | 0 | 0 | 0 | 0 | 0 | 0 | 0 |
| | | | Moribundity | 0 | 0 | 0 | 0 | 0 | 0 | 0 | 0 | 0 | 0 | 0 | 0 |
| | | | Death | 0 | 0 | 0 | 0 | 0 | 0 | 0 | 0 | 0 | 0 | 0 | 0 |
| EF-2001 | 1.6 | 29 | Number of animals | 9 | 9 | 9 | 9 | 9 | 9 | 9 | 9 | 9 | 9 | 9 | 9 |
| | | | Normal | 9 | 9 | 9 | 9 | 9 | 9 | 9 | 9 | 9 | 9 | 9 | 9 |
| | | | Loose stool | 0 | 0 | 0 | 0 | 0 | 0 | 0 | 0 | 0 | 0 | 0 | 0 |
| | | | Coarse fur | 0 | 0 | 0 | 0 | 0 | 0 | 0 | 0 | 0 | 0 | 0 | 0 |
| | | | Death | 0 | 0 | 0 | 0 | 0 | 0 | 0 | 0 | 0 | 0 | 0 | 0 |
| | | 22 | Number of animals | 8 | 8 | 8 | 8 | 8 | 8 | 8 | 8 | 8 | 8 | 8 | 8 |
| | | | Normal | 8 | 8 | 8 | 8 | 8 | 8 | 8 | 8 | 8 | 8 | 8 | 8 |
| | | | Loose stool | 0 | 0 | 0 | 0 | 0 | 0 | 0 | 0 | 0 | 0 | 0 | 0 |
| | | | Coarse fur | 0 | 0 | 0 | 0 | 0 | 0 | 0 | 0 | 0 | 0 | 0 | 0 |
| | | | Death | 0 | 0 | 0 | 0 | 0 | 0 | 0 | 0 | 0 | 0 | 0 | 0 |

[a]Start of administration.
AM1: 1st observation in the morning, AM2: 2nd observation in the morning, PM1: 1st observation in the afternoon, PM2: 2nd observation in the afternoon.
AM: Morning, PM: Afternoon.

Body Weight

The results are shown in FIG. 2.

In the control group, the mean body weight decreased at day 1 post-inoculation, but thereafter increased steadily.

In both the whole-period administration group and the post-inoculation administration group, the mean body weight increased steadily as in the control group.

Feed Intake

The results are shown in FIG. 3.

In the control group, the mean feed intake decreased transiently 2 days before inoculation (the day after the initial administration of clindamycin), but recovered thereafter.

In the whole-period administration group, animals took feed in the same manner as in the control group.

In the post-inoculation administration group, animals took feed in the same manner as in the control group. At day 5 post-inoculation, significantly high values were recognized as compared to the control group.

Water Intake

The results are shown in FIG. 4.

In the control group, the mean water intake decreased transiently 2 days before inoculation (the day after the initial administration of clindamycin). The subsequent trend of the mean water intake was the same as before the administration of clindamycin, with some variations, though.

In both the whole-period administration group and the post-inoculation administration group, the mean water intake was almost equal to that of the control group.

Viable Cell Count in the Stool

The results are shown in FIG. 5-1 to FIG. 5-4.

No viable cells were detected in the stool in any of the groups the day before inoculation (FIG. 5-1).

At day 1 post-inoculation, viable cell count in the stool was $53.6 \pm 6.4 \times 10^3$ CFU/mL in the control group, $21.6 \pm 1.6 \times 10^3$ CFU/mL in the whole-period administration group, and $39.3 \pm 3.3 \times 10^3$ CFU/mL in the post-inoculation administration group (FIG. 5.2). Significantly low values were observed in the whole-period administration group as compared to the control group, whereas significantly high vales were observed in the post-inoculation administration group as compared to the whole-period administration group.

At day 4 post-inoculation, viable cell count in the stool was 397.4±50.6×10³ CFU/mL in the control group, 16.0±4.9×10³ CFU/mL in the whole-period administration group, and 19.7±4.5×10³ CFU/mL in the post-inoculation administration group (FIG. 5-3). Significantly low values were recognized in the whole-period administration group and the post-inoculation administration group, as compared to the control group.

At day 22 post-inoculation, viable cell count in the stool was 2.1×10³ CFU/mL in the control group, 0.4±0.3×10³ CFU/mL in the whole-period administration group, and 0.7±0.3×10³ CFU/mL in the post-inoculation administration group (FIG. 5-4).

(Discussion)

A lactic acid bacterium-containing drink was orally administered to *C. difficile* infection model, whereby the effect of the timing of the start of administration upon phylaxis of *C. difficile* infection was evaluated with indicators such as survival rate in order to examine the most efficient intake conditions.

Although loose stool was observed in every animal, piloerection was observed only in a very small number of animals (1 out of 10 cases or 2 out of 10 cases) when the lactic acid bacterium powder was administered, whereas every animal in the control group exhibited piloerection.

The survival rate was 20% in the control group (8 out of 10 cases died), whereas it was 90% in the whole-period administration group (1 out of 10 cases died), and 80% in the post-inoculation administration group (2 out of 10 cases died), showing a significant rise in survival rate due to the administration of the lactic acid bacterium powder.

The viable cell count in the stool at day 1 post-inoculation decreased in this order: the control group>the post-inoculation administration group>the whole-period administration group. A difference was observed between the lactic acid bacterium powder administration groups. Both at day 4 post-inoculation and at day 22 post-inoculation, administration groups exhibited lower values than the control group, but no difference was observed between the administration groups.

Changes in body weight, feed intake and water intake saw similar trends in the administration groups and the control group. No difference was observed in the administration groups.

From the foregoing, it has been demonstrated that intake of lactic acid bacterium powder EF-2001 (a component of the lactic acid bacterium-containing drink) is the most effective for phylaxis if its ingestion is started before *C. difficile* infection and continued after such infection. Even when the bacterium powder was ingested after inoculation of *C. difficile*, an effect upon phylaxis was observed.

All publications, patents and patent applications cited herein are incorporated herein by reference in their entirety.

INDUSTRIAL APPLICABILITY

The present invention is applicable to prevention and/or treatment of *Clostridium difficile* infection.

The invention claimed is:

1. A method of treating *Clostridium difficile* infection in a subject in need thereof, comprising administering to the subject a pharmaceutically effective amount of EF-2001 strain of *Enterococcus faecalis* that is killed.

2. The method according to claim 1, wherein the EF-2001 strain of *Enterococcus faecalis* is orally administered.

3. The method according to claim 1, wherein the EF-2001 strain of *Enterococcus faecalis* is orally administered in an amount of $1\times10^8$-$1\times10^{11}$ CFU/kg body weight per dose.

4. The method according to claim 1, wherein the EF-2001 strain of *Enterococcus faecalis* is orally administered one or more times per day in an amount of $1\times10^8$-$1\times10^{11}$ CFU/kg body weight per dose.

5. The method according to claim 1, wherein the EF-2001 strain of *Enterococcus faecalis* is orally administered one to five times per day in an amount of $1\times10^8$-$1\times10^{11}$ CFU/kg body weight per dose.

6. The method according to claim 1, wherein the EF-2001 strain of *Enterococcus faecalis* is orally administered in an amount of $1\times10^9$-$5\times10^{10}$ CFU/kg body weight per dose.

7. The method according to claim 1, wherein the EF-2001 strain of *Enterococcus faecalis* is orally administered one or more times per day in an amount of $1\times10^9$-$5\times10^{10}$ CFU/kg body weight per dose.

8. The method according to claim 1, wherein the EF-2001 strain of *Enterococcus faecalis* is orally administered one to five times per day in an amount of $1\times10^9$-$5\times10^{10}$ CFU/kg body weight per dose.

9. The method according to claim 1, wherein the EF-2001 strain of *Enterococcus faecalis* is orally administered in an amount of $1.2\times10^{10}$ or more CFU/kg body weight per dose.

10. The method according to claim 1, wherein the EF-2001 strain of *Enterococcus faecalis* is orally administered one or more times per day in an amount of $1.2\times10^{10}$ or more CFU/kg body weight per dose.

11. The method according to claim 1, wherein the EF-2001 strain of *Enterococcus faecalis* is orally administered one to five times per day in an amount of $1.2\times10^{10}$ or more CFU/kg body weight per dose.

12. The method according to claim 1, the EF-2001 strain of *Enterococcus faecalis* is orally administered for seven or more days.

13. The method according to claim 1, wherein the method induces the immune response in the subject.

14. The method according to claim 1, wherein the EF-2001 strain of *Enterococcus faecalis* is administered as a mixture comprising one or more selected from the group consisting of a liquid carrier, a solid carrier, a lubricant, a binder, a disintegrant, an antioxidant, a colorant, a flavoring agent, a preservative, and a combination thereof.

15. The method according to claim 14, wherein the mixture is prepared as a tablet, a capsule, a powder, a granule, a liquid, a syrup, an aerosol, a suppository, or an injection.

16. The method according to claim 1, wherein the EF-2001 strain of *Enterococcus faecalis* is nasally administered.

17. The method according to claim 1, wherein the EF-2001 strain of *Enterococcus faecalis* is rectally administered.

18. The method according to claim 1, wherein the EF-2001 strain of *Enterococcus faecalis* is subcutaneously administered.

* * * * *